(12) United States Patent
Steagall et al.

(10) Patent No.: US 11,465,954 B2
(45) Date of Patent: Oct. 11, 2022

(54) METHODS FOR REMOVING FLUORIDE COMPOUNDS IN LIQUID HYDROCARBON MIXTURES

(71) Applicant: Shamrock Petrochemical Consulting, LLC, Houston, TX (US)

(72) Inventors: David Shane Steagall, Houston, TX (US); John David Cook, Baytown, TX (US)

( * ) Notice: Subject to any disclaimer, the term of this patent is extended or adjusted under 35 U.S.C. 154(b) by 129 days.

(21) Appl. No.: 16/860,870

(22) Filed: Apr. 28, 2020

(65) Prior Publication Data

US 2020/0339491 A1    Oct. 29, 2020

Related U.S. Application Data

(60) Provisional application No. 62/840,251, filed on Apr. 29, 2019.

(51) Int. Cl.
*C07C 7/12* (2006.01)

(52) U.S. Cl.
CPC ..................................... *C07C 7/12* (2013.01)

(58) Field of Classification Search
CPC .... C07C 7/12; C07C 7/13; C07C 9/10; C07C 19/08; C07C 17/38; C07C 2527/1206; C07C 2/62; B01J 27/02; B01J 39/14; B01D 2253/104; B01D 2256/24; B01D 2257/206; B01D 2259/40086; B01D 53/08

See application file for complete search history.

(56) References Cited

U.S. PATENT DOCUMENTS 5,396,022 A * 3/1995 Wu .................. C07C 7/1485
585/733
8,487,155 B2 * 7/2013 Boateng .................. B01J 39/09
585/820

* cited by examiner

*Primary Examiner* — Sharon Pregler

(57) ABSTRACT

The present disclosure relates to methods of de-fluorinating hydrocarbon mixtures using an aluminum oxide containing resin. Benefits of the methods disclosed herein can include effective and time efficient removal of fluorine compounds from mixtures of hydrocarbons at ambient temperatures.

16 Claims, 1 Drawing Sheet

METHODS FOR REMOVING FLUORIDE COMPOUNDS IN LIQUID HYDROCARBON MIXTURES

CROSS-REFERENCE TO RELATED APPLICATIONS

This application claims priority to U.S. Provisional Application No. 62/840,251, filed Apr. 29, 2019, which is incorporated by reference in its entirety.

TECHNICAL FIELD

The present disclosure relates to methods of de-fluorinating hydrocarbon mixtures using an aluminum oxide containing resin. Benefits of the methods disclosed herein can include effective and time efficient removal of fluorine compounds from mixtures of hydrocarbons at ambient temperatures.

BACKGROUND

Alkylation reactions catalyzed by hydrofluoric acid (HF) are widely used by refineries to combine unsaturated light hydrocarbons to produce high octane hydrocarbons for use in gasoline fuels. The hydrocarbon streams resulting from HF-catalyzed alkylation reactions frequently contain high levels of corrosive and toxic fluorine compounds including HF, presenting challenges for removal of these compounds from the reaction products. There remains a need in the art for effective methods for removal of fluorine compounds from hydrocarbon mixtures.

SUMMARY

Embodiments herein are directed to methods of de-fluorinating a hydrocarbon mixture. In various embodiments, such a method includes providing a hydrocarbon mixture containing at least one fluorine compound, providing an aluminum oxide containing resin, wherein the aluminum oxide containing resin contains less than about 0.1 weight percent sulfur; and contacting the hydrocarbon mixture with the aluminum oxide containing resin at an ambient temperature to form a de-fluorinated hydrocarbon mixture. In certain embodiments, the ambient temperature is from about 15 degrees Celsius to about 30 degrees Celsius.

In certain embodiments, the hydrocarbon mixture includes alkanes containing from 3 to 16 carbon atoms per molecule. In certain embodiments, the hydrocarbon mixture contains about 99 percent butane or heavier, about 13 percent hexane or heavier, or about 55 percent pentane or heavier. In certain embodiments, the hydrocarbon mixture is in a liquid state when contacted with the aluminum oxide containing resin. In various embodiments, the at least one fluorine compound includes HF. In certain embodiments, the HF is present in the hydrocarbon mixture at a concentration of from about 300 ppm to about 600 ppm or higher.

In various embodiments, the at least one fluorine compound is adsorbed by the aluminum oxide containing resin to de-fluorinate the hydrocarbon mixture; in certain embodiments, the de-fluorinated hydrocarbon mixture contains about 1 ppm or less of HF.

In certain embodiments of the methods disclosed herein, the aluminum oxide containing resin contains about 75% or more of activated alumina. In certain embodiments, the aluminum oxide containing resin contains about 75% or more of a zeolite mineral. In certain embodiments, the aluminum oxide containing resin contains about 25% or less of a clay binder. In certain embodiments, the aluminum oxide containing resin adsorbs from about 40% to about 60% or more of the HF in a liquid state. In certain embodiments, the hydrocarbon mixture is in contact with the aluminum oxide containing resin for an average residence time of from about 10 minutes to about 20 minutes.

Embodied methods of de-fluorinating a hydrocarbon mixture herein include providing a hydrocarbon mixture containing at least one fluorine compound; providing at least one treater vessel containing an aluminum oxide containing resin, wherein the aluminum oxide containing resin contains less than about 0.1 weight percent sulfur; and pumping the hydrocarbon mixture through the at least one treater vessel at an ambient temperature, wherein the hydrocarbon mixture contacts the aluminum oxide containing resin at the ambient temperature to form a de-fluorinated hydrocarbon mixture. In various embodiments, the at least one fluorine compound is adsorbed by the aluminum oxide containing resin to de-fluorinate the hydrocarbon mixture.

In embodiments of methods herein, each of the at least one treater vessel has a pressure of from about 206 kpa to about 551 kpa. In certain embodiments, the hydrocarbon mixture flows through the at least one treater vessel at a flow rate of from about 50 gpm to about 400 gpm or a residence time of from about 10 minutes to about 20 minutes or more. In certain embodiments, the hydrocarbon mixture pumped through the at least one treater vessel comprises alkanes containing from 3 to 16 carbon atoms per molecule In certain embodiments, the hydrocarbon mixture contains about 99 percent butane or heavier, about 13 percent hexane or heavier, or about 55 percent pentane or heavier. In certain embodiments, the hydrocarbon mixture is in a liquid state when contacted with the aluminum oxide containing resin. In various embodiments, the fluorine compound includes HF; in various embodiments, the HF is present in the hydrocarbon mixture at a concentration of from about 300 ppm to about 600 ppm or higher. In certain embodiments, the ambient temperature is from about 15 degrees Celsius to about 30 degrees Celsius. In certain embodiments, the de-fluorinated hydrocarbon mixture contains about 1 ppm or less of HF. In certain embodiments, the aluminum oxide containing resin contains about 75% or more of activated alumina. In certain embodiments, the aluminum oxide containing resin contains about 75% or more of a zeolite mineral. In certain embodiments, the aluminum oxide containing resin contains about 25% or less of a clay binder. In certain embodiments, the aluminum oxide containing resin adsorbs from about 40% to about 60% or more of the HF in a liquid state. In certain embodiments, the hydrocarbon mixture is in contact with the aluminum oxide containing resin contained in the at least one treater vessel for an average residence time of about 10 to 20 minutes or less. In certain embodiments, the hydrocarbon mixture is pumped through at least two treater vessels. In certain embodiments, the at least two treater vessels are connected in a serial configuration.

Embodiments of methods herein include providing a first treater vessel and a last treater vessel, and further including a first filter connected to the first treater vessel and a second filter connected to the last treater vessel, wherein the hydrocarbon mixture is passed through the first filter before being pumped into the first treater vessel, and wherein the de-fluorinated hydrocarbon mixture is passed through the second filter after being pumped through the last treater vessel.

Embodiments of methods of de-fluorinating an alkane mixture disclosed herein include providing at least two treatment vessels containing an aluminum oxide containing resin, wherein the at least two treatment vessels are connected in a serial configuration, and wherein the aluminum oxide contains less than about 0.1 weight percent sulfur; feeding an alkane mixture containing at least one fluorine compound from a first storage tank through a pump into the at least two treater vessels, wherein the alkane mixture is in a liquid state and at an ambient temperature, and wherein the alkane mixture is fed into the at least two treater vessels at a flow rate of from about 60 gpm to about 400 gpm; contacting the alkane mixture with the aluminum oxide containing resin at a pressure of from about 206 kpa to about 551 kpa at the ambient temperature in the at least two treater vessels, wherein the alkane mixture has an average residence time of contact with the aluminum oxide containing resin of about 15 minutes or less; and collecting a de-fluorinated alkane mixture from the at least two treater vessels through a finished product line into a second storage tank. In certain embodiments, the alkane mixture is fed from a reactor vessel into the first storage tank. In certain embodiments, the at least one fluorine compound is adsorbed by the aluminum oxide containing resin to de-fluorinate the alkane mixture. In certain embodiments, the alkane mixture comprises alkanes containing from 3 to 16 carbon atoms per molecule. In certain embodiments, the alkane mixture contains about 99 percent butane or heavier, about 13 percent hexane or heavier, or about 55 percent pentane or heavier. In certain embodiments, the fluorine compound includes HF. In certain embodiments, the HF is present in the alkane mixture at a concentration of from about 300 ppm to about 600 ppm or higher. In certain embodiments, the ambient temperature is from about 15 degrees Celsius to about 30 degrees Celsius. In certain embodiments, the de-fluorinated hydrocarbon mixture contains about 1 ppm or less of HF. In certain embodiments, the aluminum oxide containing resin contains about 75% or more of activated alumina. In certain embodiments, the aluminum oxide containing resin contains about 75% or more of a zeolite mineral. In certain embodiments, the aluminum oxide containing resin contains about 25% or less of a clay binder. In certain embodiments, the aluminum oxide containing resin adsorbs from about 40% to about 60% or more of the HF in a liquid state.

Certain embodiments of the methods herein include providing from two treater vessels to about five treater vessels, wherein the treater vessels are provided in a substantially horizontal configuration on a vehicle rig platform, or the first and last treater vessels are a single vessel. Certain embodiments include providing a first treater vessel a last treater vessel, and further providing a first filter connected to the first treater vessel and a second filter connected to the last treater vessel, wherein the alkane mixture is passed through the first filter before being pumped into the first treater vessel, and wherein the de-fluorinated alkane mixture is passed through the second filter after being pumped through the last treater vessel.

BRIEF DESCRIPTION OF THE DRAWINGS

The foregoing summary, as well as the following detailed description of the embodiments, will be better understood when read in conjunction with the attached drawings. For the purpose of illustration, there are shown in the drawings some embodiments, which may be preferable. It should be understood that the embodiments depicted are not limited to the precise details shown. Unless otherwise noted, the drawings are not to scale.

DETAILED DESCRIPTION

Figure 1:
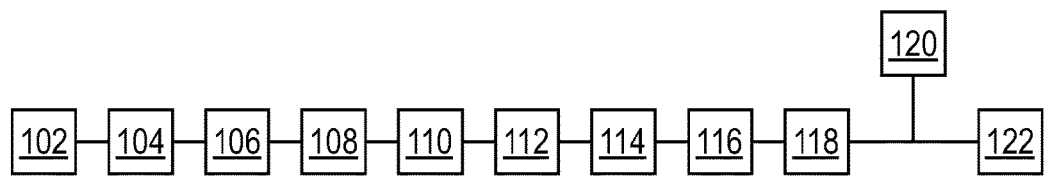
FIG. 1 is a schematic depiction of an embodiment of the system and methods disclosed herein.

Unless otherwise noted, all measurements are in standard metric units.

Unless otherwise noted, all instances of the words "a," "an," or "the" can refer to one or more than one of the word that they modify.

Unless otherwise noted, the phrase "at least one of" means one, or more than one of an object. For example, "at least one fluorine compound" means one fluorine compound, more than one fluorine compound, or any combination thereof.

Unless otherwise noted, the term "about" refers to ±10% of the non-percentage number that is described, rounded to the nearest whole integer. For example, about 300 ppm, would include 270 to 330 ppm. Unless otherwise noted, the term "about" refers to ±5% of a percentage number. For example, about 75% would include 71 to 79%. When the term "about" is discussed in terms of a range, then the term refers to the appropriate amount less than the lower limit and more than the upper limit. For example, from about 40% to about 60% would include from 36% to 66%.

Unless otherwise noted, properties (height, width, length, ratio etc.) as described herein are understood to be averaged measurements.

HF catalyzed alkylation processes are currently in use to produce high octane hydrocarbons from unsaturated light hydrocarbons. HF is preferred over sulfuric acid as a catalyst for alkylation reactions because of its greater efficiency. However, the products of HF catalyzed reactions often contain high levels of fluorine containing compounds, which must be removed before the products can be used in fuels. The products may contain high levels of corrosive and toxic HF, presenting considerable safety risks for working with and transporting materials containing HF.

Current purification methods using aluminum oxide or other metal oxide materials to remove fluorine compounds from hydrocarbon mixtures present challenges with regard to efficiency and effectiveness. Under conventional methods, the contaminated hydrocarbon mixture is processed as temperatures of around 200 Celsius, and then passed through an aluminum oxide column to remove fluorine compounds. However, the metal oxide material often becomes partially or completely spent during the purification process, so that the purification system becomes overwhelmed, and the fluorine compounds are not be removed from the hydrocarbon mixtures to acceptably low levels. To avoid the processing costs of replacing the aluminum oxide column, it is common to continue the process and produce hydrocarbons with unacceptably high amounts of fluorine compounds, and to sell the contaminated hydrocarbons at a discount (or combine with low fluoride concentrated hydrocarbons when blending economics are favorable). Another source of contamination can include the formation of channels in the metal oxide material bed, through which the hydrocarbon mixture flows without sufficient contact with the material, allowing fluorine compounds to pass through into the product stream.

In more detail, HF catalyzed reactions are currently used in the production of octane. The distillation residue contains a hydrocarbon mixture of butane and other hydrocarbons, and fluorine containing compounds as contaminants. The hydrocarbon mixtures can be purified of fluorine contaminants by passing the mixtures through aluminum oxide containing columns at temperatures as high as 200 Celsius. However due to the speed at which the hydrocarbon mixtures are run through the aluminum oxide columns, the purified mixtures still typically contain high contaminating levels of HF.

Because slowing the purification process down enough to effectively remove the HF is prohibitive in terms of time and cost, the contaminated hydrocarbon mixtures are sold at a large discount. Shipment of the hydrocarbon mixtures elsewhere for treatment is also cost prohibitive, due to the risks associated with the hazardous nature of HF.

Embodiments of the present disclosure can provide methods to de-fluorinate hydrocarbon mixtures to acceptably low fluorine compound levels, usually 1 ppm or less, using an aluminum oxide containing resin. It has been discovered that the methods disclosed herein can remove excess fluorine compounds from a contaminated hydrocarbon mixture after conventional processing by contacting the contaminated hydrocarbon mixture with an aluminum oxide containing resin at ambient temperatures. Embodiments herein can provide a benefit of removing fluorine compounds from hydrocarbon mixtures that are in a liquid state. A benefit of such methods can include the removal of fluorine compounds from previously unusable hydrocarbon mixtures to acceptably low levels in a time efficient and cost effective manner. Embodiments herein can provide a benefit of the use of treatment vessels for de-fluorination of hydrocarbon mixtures provided on a vehicle rig platform. Such embodiments can provide an advantage of allowing services for de-fluorination treatment of hydrocarbon mixtures to be delivered at a refinery location.

Referring to FIG. 1, in an embodiment, the method uses a system as shown. An untreated hydrocarbon mixture containing at least one fluorine compound can be stored in storage tank 102. The hydrocarbon mixture can be fed through a first filter 104 and pumped through pump 106 into from one to five treater vessels 108, 110, 112, 114, and 116 connected in series. The treated hydrocarbon mixture can be fed through second filter 118, and collected through finished product line 120 into treated product storage tank 122.

Figure 2:
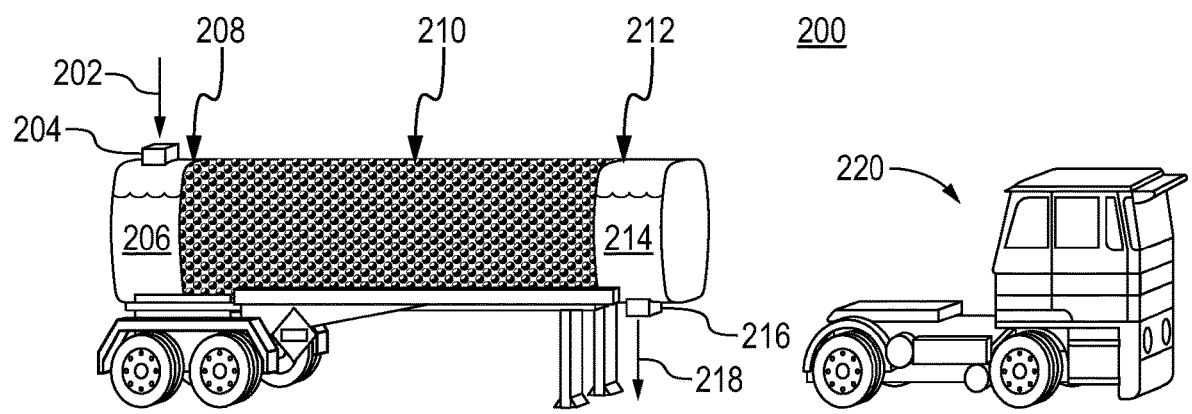
FIG. 2 is a schematic depiction of an embodiment of the system and methods disclosed herein.

Referring to FIG. 2, in an embodiment, the method uses a de-fluorination and transport system 200. A hydrocarbon mixture containing at least one fluorine compound can be treated by de-fluorination system 202. The untreated hydrocarbon mixture can be fed through inlet 204 into storage tank 206. The hydrocarbon mixture can be passed through filter 208 into treater vessel 210 containing an aluminum oxide resin. The treated hydrocarbon mixture can be passed through filter 212 into storage tank 214. The treated product 218 can be collected from storage tank 214 through outlet 216. The de-fluorination system 202 can be transported on vehicle rig platform 220.

Embodiments of Methods of De-Fluorinating Hydrocarbon Mixtures

Embodied methods of de-fluorinating a hydrocarbon mixture as disclosed herein can include providing a hydrocarbon mixture containing at least one fluorine compound. In various embodiments herein, the hydrocarbon mixture can include alkanes containing from 3 to 16 carbon atoms per molecule. In some embodiments, the hydrocarbon mixture can include alkanes containing from 5 to 14 carbon atoms per molecule. In some embodiments, the hydrocarbon mixture can include alkanes containing from 7 to 12 carbon atoms per molecule. In an embodiment, the hydrocarbon mixture can contain about 99 percent butane or heavier, about 13 percent hexane or heavier, or about 55 percent pentane or heavier. In various embodiments, the at least one fluorine compound in the hydrocarbon mixture can include HF. In some embodiments, the HF is present in the hydrocarbon mixture at a concentration of from about 300 ppm to about 600 ppm or higher. In some embodiments, the HF is present in the hydrocarbon mixture at a concentration of from about 200 ppm to about 600 ppm or higher. In some embodiments, the HF is present in the hydrocarbon mixture at a concentration of from about 100 ppm to about 600 ppm or higher.

Embodied methods can provide an aluminum oxide containing resin; in various embodiments, the aluminum oxide containing resin contains less than about 0.1 weight percent sulfur. In various embodiments, the hydrocarbon mixture is contacted with the aluminum oxide containing resin at an ambient temperature to form a de-fluorinated hydrocarbon mixture. In various embodiments, the ambient temperature can be from about 15 degrees Celsius to about 30 degrees Celsius. In some embodiments, the ambient temperature can be from about 20 degrees Celsius to about 25 degrees Celsius. In various embodiments, the at least one fluorine compound is adsorbed by the aluminum oxide containing resin to de-fluorinate the hydrocarbon mixture.

In various embodiments, the hydrocarbon mixture can be in contact with the aluminum oxide containing resin for an average residence time of from about 10 minutes to about 20 minutes or more. In some embodiments, the hydrocarbon mixture can be in contact with the aluminum oxide resin for an average residence time of from about 12 minutes to about 18 minutes. In some embodiments, the hydrocarbon mixture can be in contact with the aluminum oxide resin for an average residence time of from about 14 minutes to about 16 minutes. In an embodiment, the hydrocarbon mixture can be in a liquid state when contacted with the aluminum oxide containing resin. In an embodiment, the aluminum oxide containing resin adsorbs from about 40% to about 60% or more of the HF in a liquid state. In some embodiments, the aluminum oxide containing resin adsorbs from about 45% to about 55% of the HF in a liquid state. In an embodiment, the de-fluorinated hydrocarbon mixture contains about 1 ppm or less of HF.

Embodied methods of de-fluorinating a hydrocarbon mixture herein can include providing a hydrocarbon mixture containing at least one fluorine compound, and at least one treater vessel containing an aluminum oxide containing resin, wherein the aluminum oxide containing resin contains less than about 0.1 weight percent sulfur. In an embodiment, the hydrocarbon mixture can include alkanes containing from 3 to 16 carbon atoms per molecule. In some embodiments, the hydrocarbon mixture can include alkanes containing from 5 to 14 carbon atoms per molecule. In some embodiments, the hydrocarbon mixture can include alkanes containing from 7 to 12 carbon atoms per molecule. In an embodiment, the hydrocarbon mixture can contain about 99% butane or heavier, about 13% hexane or heavier, or about 55% pentane or heavier. In an embodiment, the at least one fluorine compound includes HF. In some embodiments, the HF is present in the hydrocarbon mixture at a concentration of from about 300 ppm to about 600 ppm or higher. In some embodiments, the HF is present in the hydrocarbon mixture at a concentration of from about 200 ppm to about 600 ppm or higher. In some embodiments, the HF is present in the hydrocarbon mixture at a concentration of from about 100 ppm to about 600 ppm or higher.

In various embodiments, the hydrocarbon mixture can be pumped through the at least one treater vessel at an ambient temperature, which in some embodiments can include an ambient temperature from about 15 degrees Celsius to about 30 degrees Celsius. In some embodiments, the ambient temperature can be from about 20 degrees Celsius to about 25 degrees Celsius. In such embodiments, a treater vessel can have the form of a tank, such as a steel tank, a polisher, scrubber, or a column, which can contain an aluminum oxide containing resin, and through which the hydrocarbon mixture can be pumped at an ambient temperature, according to embodied methods. In such embodiments, the hydrocarbon mixture contacts the aluminum oxide containing resin at the ambient temperature to form a de-fluorinated hydrocarbon mixture. In an embodiment, the at least one fluorine compound is adsorbed by the aluminum oxide containing resin to de-fluorinate the hydrocarbon mixture. In an embodiment, each of the at least one treater vessel has a pressure of from about 206 kpa to about 551 kpa. In some embodiments, each of the at least one treater vessel has a pressure of from about 250 kpa to about 500 kpa. In some embodiments, each of the at least one treater vessel has a pressure of from about 300 kpa to about 400 kpa. In an embodiment, the hydrocarbon mixture flows through the at least one treater vessel at a flow rate of from about 50 gpm to about 400 gpm. In some embodiments, the hydrocarbon mixture flows through the at least one treater vessel at a flow rate of from about 100 gpm to about 300 gpm. In some embodiments, the hydrocarbon mixture flows through the at least one treater vessel at a flow rate of from about 150 gpm to about 250 gpm. In an embodiment, the average residence time the hydrocarbon mixture is in contact with the aluminum oxide containing resin is from about 10 minutes to about 20 minutes or more. In another embodiment, the hydrocarbon mixture is in contact with the aluminum oxide containing resin for an average residence time of from about 10 minutes to 20 minutes or less. In an embodiment, the hydrocarbon mixture is in a liquid state when contacted with the aluminum oxide containing resin. In an embodiment, the de-fluorinated hydrocarbon mixture contains about 1 ppm or less of HF.

In some embodiments, the hydrocarbon mixture is pumped through at least two treater vessels. In such embodiments, the at least two treater vessels can be connected in a serial configuration. Such embodiments can provide a benefit to the disclosed methods of redundancy, helping to increase the degree of contact of the hydrocarbon mixture with the aluminum oxide containing resin, and reduce flow through of the at least one fluorine compound with the de-fluorinated mixture. Such embodiments can provide a benefit of reducing the effects of a treater vessel becoming saturated or overwhelmed by the amount of fluorine compounds in a hydrocarbon mixture. In some embodiments, the at least one treater vessel can include a first treater vessel and a last treater vessel. In such embodiments, a first filter can be connected to the first treater vessel, and a second filter can be connected to the last treater vessel. In such embodiments, the hydrocarbon mixture can be passed through the first filter before being pumped into the first treater vessel. Such embodiments can provide a benefit to the methods of filtering contaminants out of a hydrocarbon mixture before the hydrocarbon mixture is contacted with the aluminum oxide containing resin. In some embodiments, the de-fluorinated hydrocarbon mixture can be passed through a second filter after being pumped through the last treater vessel. Such embodiments can provide a benefit to the embodied methods of filtering any aluminum oxide containing resin from the de-fluorinated hydrocarbon mixture.

Embodiments of methods of de-fluorinating an alkane mixture herein can include providing at least two treater vessels containing an aluminum oxide containing resin. In an embodiment, the aluminum oxide containing resin includes less than about 0.1 weight percent sulfur. In an embodiment, the method includes from two treater vessels to about five treater vessels. In an embodiment, the treater vessels can be connected in a serial configuration. In such embodiments, an alkane mixture containing at least one fluorine compound can be fed into the at least two treater vessels from a first storage tank through a pump, where the alkane mixture is in a liquid state and at an ambient temperature. In an embodiment, the alkane mixture can include alkanes containing from 3 to 16 carbon atoms per molecule. In some embodiments, the hydrocarbon mixture can include alkanes containing from 5 to 14 carbon atoms per molecule. In some embodiments, the hydrocarbon mixture can include alkanes containing from 7 to 12 carbon atoms per molecule. In an embodiment, the alkane mixture contains about 99% butane or heavier, about 13% hexane or heavier, or about 55% pentane or heavier. In an embodiment, the at least one fluorine compound can include HF. In such embodiments, the HF can be present in the alkane mixture at a concentration of from about 300 ppm to about 600 ppm or higher. In some embodiments, the HF is present in the hydrocarbon mixture at a concentration of from about 200 ppm to about 600 ppm or higher. In some embodiments, the HF is present in the hydrocarbon mixture at a concentration of from about 100 ppm to about 600 ppm or higher. In such embodiments, the ambient temperature can include from about 15 degrees Celsius to about 30 degrees Celsius. In some embodiments, the ambient temperature can be from about 20 degrees Celsius to about 25 degrees Celsius.

In an embodiment, the alkane mixture can be fed into the at least two treater vessels at a flow rate of from about 60 gpm to about 400 gpm. In some embodiments, the hydrocarbon mixture flows through the at least one treater vessel at a flow rate of from about 100 gpm to about 300 gpm. In some embodiments, the hydrocarbon mixture flows through the at least one treater vessel at a flow rate of from about 150 gpm to about 250 gpm. In an embodiment, the alkane mixture can be contacted with the aluminum oxide containing resin at a pressure of from about 206 kpa to about 551 kpa at an ambient temperature in the at least two treater vessels. In some embodiments, each of the at least one treater vessel has a pressure of from about 250 kpa to about 500 kpa. In some embodiments, each of the at least one treater vessel has a pressure of from about 300 kpa to about 400 kpa. In such embodiments, the at least one fluorine compound is adsorbed by the aluminum oxide containing resin to de-fluorinate the alkane mixture. In an embodiment, the alkane mixture can have an average residence time of contact with the aluminum oxide containing resin of about 15 minutes or less. In an embodiment, the alkane mixture can have an average residence time of contact with the aluminum oxide containing resin of about 20 minutes or less. In an embodiment, the aluminum oxide containing resin adsorbs from about 40% to about 60% or more of the HF in a liquid state. In such embodiments, a de-fluorinated alkane mixture can be collected from the at least two treater vessels through a finished product line into a second storage tank. In some embodiments, the de-fluorinated alkane mixture contains about 1 ppm or less of HF.

In some embodiments, the at least two treater vessels can include a first treater vessel and a last treater vessel, a first filter connected to the first treater vessel, and a second filter connected to the last treater vessel. In such embodiments, an alkane mixture can be passed through the first filter before being pumped into the first treater vessel, and the de-fluorinated alkane mixture can be passed through the second filter after being pumped through the last treater vessel. In another embodiment, the first and last treater vessels can be a single vessel.

In an embodiment, the alkane mixture can be fed from a reactor vessel into the first storage tank. In an embodiment, from two treater vessels to about five treater vessels, or a single treater vessel, can be provided in a substantially horizontal configuration on a vehicle rig platform. A substantially horizontal configuration of the treater vessels can provide a benefit to the embodied methods of avoiding a crushing or powdering of the alumina containing resin that can occur in a vertical configuration. An embodiment of a vehicle rig platform can include a substantially flat truck bed. Such embodiments can provide an advantage to the methods of providing de-fluorination treatment of alkane mixtures at a refinery location where HF catalyzed alkylation reactions are performed, and avoiding the necessity of transport of fluorine contaminated alkane mixtures elsewhere for de-fluorination.

Aluminum Oxide Containing Resins of Various Embodiments

It has been surprisingly discovered that it is possible to remove fluorine compounds from hydrocarbon mixtures at ambient temperatures by contacting the hydrocarbon mixtures with aluminum oxide containing resins. Further, it has been surprisingly discovered that the aluminum oxide containing resins are effective even when less than 0.1 weight percent of sulfur is present in the aluminum oxide containing resin. Embodiments of aluminum oxide containing resins herein can include an aluminum oxide containing resin that includes less than about 0.1 weight percent sulfur. Such an aluminum oxide containing resin can include a promoted activated alumina, a regenerative adsorbent alumina, a crystalline silica, zeolite minerals, or combinations thereof. In an embodiment, the aluminum oxide containing resin can contain about 75% or more of activated alumina. In an embodiment, the aluminum oxide containing resin can contain about 65% or more of activated alumina. In an embodiment, the aluminum oxide containing resin can contain about 55% or more of activated alumina. In an embodiment, the aluminum oxide containing resin can contain about 75% or more of a zeolite mineral. In an embodiment, the aluminum oxide containing resin can contain about 65% or more of a zeolite mineral. In an embodiment, the aluminum oxide containing resin can contain about 65% or more of a zeolite mineral. In such embodiments, the aluminum oxide containing resin can include one or more aluminum silica oxides. In an embodiment, the aluminum oxide containing resin can optionally include a clay binder. In such an embodiment, the aluminum oxide containing resin can contain about 25% or less of a clay binder. In an embodiment, the aluminum oxide containing resin can contain about 20% or less of a clay binder. In an embodiment, the aluminum oxide containing resin can contain about 15% or less of a clay binder.

SOME EXEMPLARY EMBODIMENTS

Embodiment 1. A method of de-fluorinating a hydrocarbon mixture comprising:
providing a hydrocarbon mixture containing at least one fluorine compound;
providing an aluminum oxide containing resin, wherein the aluminum oxide containing resin contains less than about 0.1 weight percent sulfur; and
contacting the hydrocarbon mixture with the aluminum oxide containing resin at an ambient temperature to form a de-fluorinated hydrocarbon mixture.

Embodiment 2. The method of embodiment 1 or any other embodiment, wherein the at least one fluorine compound is adsorbed by the aluminum oxide containing resin to de-fluorinate the hydrocarbon mixture.

Embodiment 3. The method of embodiment 1 or any other embodiment, wherein the hydrocarbon mixture comprises alkanes containing from 3 to 16 carbon atoms per molecule.

Embodiment 4. The method of embodiment 3 or any other embodiment, wherein the hydrocarbon mixture contains about 99 percent butane or heavier, about 13 percent hexane or heavier, or about 55 percent pentane or heavier.

Embodiment 5. The method of embodiment 1 or any other embodiment, wherein the hydrocarbon mixture is in a liquid state when contacted with the aluminum oxide containing resin.

Embodiment 6. The method of embodiment 1 or any other embodiment, wherein the at least one fluorine compound comprises HF.

Embodiment 7. The method of embodiment 6 or any other embodiment, wherein the HF is present in the hydrocarbon mixture at a concentration of from about 300 ppm to about 600 ppm or higher.

Embodiment 8. The method of embodiment 1 or any other embodiment, wherein the ambient temperature is from about 15 degrees Celsius to about 30 degrees Celsius.

Embodiment 9. The method of embodiment 1 or any other embodiment, wherein the de-fluorinated hydrocarbon mixture contains about 1 ppm or less of HF.

Embodiment 10. The method of embodiment 1 or any other embodiment, wherein the aluminum oxide containing resin contains about 75% or more of activated alumina.

Embodiment 11. The method of embodiment 1 or any other embodiment, wherein the aluminum oxide containing resin contains about 75% or more of a zeolite mineral.

Embodiment 12. The method of embodiment 1 or any other embodiment, wherein the aluminum oxide containing resin contains about 25% or less of a clay binder.

Embodiment 13. The method of embodiment 6 or any other embodiment, wherein the aluminum oxide containing resin adsorbs from about 40% to about 60% or more of the HF in a liquid state.

Embodiment 14. The method of embodiment 1 or any other embodiment, wherein the hydrocarbon mixture is in contact with the aluminum oxide containing resin for an average residence time of from about 10 minutes to about 20 minutes.

Embodiment 15. A method of de-fluorinating a hydrocarbon mixture comprising:
providing a hydrocarbon mixture containing at least one fluorine compound;
providing at least one treater vessel containing an aluminum oxide containing resin, wherein the aluminum oxide containing resin contains less than about 0.1 weight percent sulfur; and
pumping the hydrocarbon mixture through the at least one treater vessel at an ambient temperature, wherein the hydrocarbon mixture contacts the aluminum oxide containing resin at the ambient temperature to form a de-fluorinated hydrocarbon mixture.

Embodiment 16. The method of embodiment 15 or any other embodiment, wherein the at least one fluorine compound is adsorbed by the aluminum oxide containing resin to de-fluorinate the hydrocarbon mixture.

Embodiment 17. The method of embodiment 15 or any other embodiment, wherein each of the at least one treater vessel has a pressure of from about 206 kpa to about 551 kpa.

Embodiment 18. The method of embodiment 15 or any other embodiment, wherein the hydrocarbon mixture flows through the at least one treater vessel at a flow rate of from about 50 gpm to about 400 gpm or a residence time of from about 10 minutes to about 20 minutes or more.

Embodiment 19. The method of embodiment 15 or any other embodiment, wherein the hydrocarbon mixture comprises alkanes containing from 3 to 16 carbon atoms per molecule.

Embodiment 20. The method of embodiment 19 or any other embodiment, wherein the hydrocarbon mixture contains about 99 percent butane or heavier, about 13 percent hexane or heavier, or about 55 percent pentane or heavier.

Embodiment 21. The method of embodiment 15 or any other embodiment, wherein the hydrocarbon mixture is in a liquid state when contacted with the aluminum oxide containing resin.

Embodiment 22. The method of embodiment 15 or any other embodiment, wherein the fluorine compound comprises HF.

Embodiment 23. The method of embodiment 22 or any other embodiment, wherein the HF is present in the hydrocarbon mixture at a concentration of from about 300 ppm to about 600 ppm or higher.

Embodiment 24. The method of embodiment 15 or any other embodiment, wherein the ambient temperature is from about 15 degrees Celsius to about 30 degrees Celsius.

Embodiment 25. The method of embodiment 15 or any other embodiment, wherein the de-fluorinated hydrocarbon mixture contains about 1 ppm or less of HF.

Embodiment 26. The method of embodiment 15 or any other embodiment, wherein the aluminum oxide containing resin contains about 75% or more of activated alumina.

Embodiment 27. The method of embodiment 15 or any other embodiment, wherein the aluminum oxide containing resin contains about 75% or more of a zeolite mineral.

Embodiment 28. The method of embodiment 15 or any other embodiment, wherein the aluminum oxide containing resin contains about 25% or less of a clay binder.

Embodiment 29. The method of embodiment 23 or any other embodiment, wherein the aluminum oxide containing resin adsorbs from about 40% to about 60% or more of the HF in a liquid state.

Embodiment 30. The method of embodiment 15 or any other embodiment, wherein the hydrocarbon mixture is in contact with the aluminum oxide containing resin for an average residence time of about 10 to 20 minutes or less.

Embodiment 31. The method of embodiment 15 or any other embodiment, wherein the hydrocarbon mixture is pumped through at least two treater vessels.

Embodiment 32. The method of embodiment 31 or any other embodiment, wherein the at least two treater vessels are connected in a serial configuration.

Embodiment 33. The method of embodiment 32 or any other embodiment, comprising a first treater vessel and a last treater vessel, and further comprising a first filter connected to the first treater vessel and a second filter connected to the last treater vessel, wherein the hydrocarbon mixture is passed through the first filter before being pumped into the first treater vessel, and wherein the de-fluorinated hydrocarbon mixture is passed through the second filter after being pumped through the last treater vessel.

Embodiment 34. A method of de-fluorinating an alkane mixture comprising:
providing at least two treatment vessels containing an aluminum oxide containing resin, wherein the at least two treatment vessels are connected in a serial configuration, and wherein the aluminum oxide contains less than about 0.1 weight percent sulfur;
feeding an alkane mixture containing at least one fluorine compound from a first storage tank through a pump into the at least two treater vessels, wherein the alkane mixture is in a liquid state and at an ambient temperature, and wherein the alkane mixture is fed into the at least two treater vessels at a flow rate of from about 60 gpm to about 400 gpm;
contacting the alkane mixture with the aluminum oxide containing resin at a pressure of from about 206 kpa to about 551 kpa at the ambient temperature in the at least two treater vessels, wherein the alkane mixture has an average residence time of contact with the aluminum oxide containing resin of about 15 minutes or less; and
collecting a de-fluorinated alkane mixture from the at least two treater vessels through a finished product line into a second storage tank.

Embodiment 35. The method of embodiment 34 or any other embodiment, comprising from two treater vessels to about five treater vessels, wherein the treater vessels are provided in a substantially horizontal configuration on a vehicle rig platform, or the first and last treater vessels are a single vessel.

Embodiment 36. The method of embodiment 34 or any other embodiment, comprising a first treater vessel a last treater vessel, and further comprising a first filter connected to the first treater vessel and a second filter connected to the last treater vessel, wherein the alkane mixture is passed through the first filter before being pumped into the first treater vessel, and wherein the de-fluorinated alkane mixture is passed through the second filter after being pumped through the last treater vessel.

Embodiment 37. The method of embodiment 34 or any other embodiment, wherein the alkane mixture is fed from a reactor vessel into the first storage tank.

Embodiment 38. The method of embodiment 34 or any other embodiment, wherein the at least one fluorine compound is adsorbed by the aluminum oxide containing resin to de-fluorinate the alkane mixture.

Embodiment 39. The method of embodiment 34 or any other embodiment, wherein the alkane mixture comprises alkanes containing from 3 to 16 carbon atoms per molecule.

Embodiment 40. The method of embodiment 39 or any other embodiment, wherein the alkane mixture contains about 99 percent butane or heavier, about 13 percent hexane or heavier, or about 55 percent pentane or heavier.

Embodiment 41. The method of embodiment 34 or any other embodiment, wherein the fluorine compound comprises HF.

Embodiment 42. The method of embodiment 41 or any other embodiment, wherein the HF is present in the alkane mixture at a concentration of from about 300 ppm to about 600 ppm or higher.

Embodiment 43. The method of embodiment 34 or any other embodiment, wherein the ambient temperature is from about 15 degrees Celsius to about 30 degrees Celsius.

Embodiment 44. The method of embodiment 34 or any other embodiment, wherein the de-fluorinated alkane mixture contains about 1 ppm or less of HF.

Embodiment 45. The method of embodiment 34 or any other embodiment, wherein the aluminum oxide containing resin contains about 75% or more of activated alumina.

Embodiment 46. The method of embodiment 34 or any other embodiment, wherein the aluminum oxide containing resin contains about 75% or more of a zeolite mineral.

Embodiment 47. The method of embodiment 34 or any other embodiment, wherein the aluminum oxide containing resin contains about 25% or less of a clay binder.

Embodiment 48. The method of embodiment 42 or any other embodiment, wherein the aluminum oxide containing resin adsorbs from about 40% to about 60% or more of the HF in a liquid state.

EXAMPLES

A hydrocarbon mixture containing approximately 600 ppm HF was pumped through a treater vessel containing an aluminum oxide containing resin (Axens 867 alumina cast number 1344-28-1, 98-100 percent aluminum oxide; Axens 913 alumina cast number; BASF product alox resin/zeolite cast number 1318-02-1; any clay binder percentage, cast number 14808-60-7). The aluminum oxide containing resin contained less than about 0.1 percent sulfur/contained no sulfur. The hydrocarbon mixture was pumped through the treater vessel at an ambient temperature of 25 degrees Celsius at a flow rate of 60 gallons per minute and a pressure of about 30 psig to about 80 psig. The residence time of contact of the hydrocarbon mixture with the aluminum oxide containing resin was 15 minutes. The resulting de-fluorinated hydrocarbon mixture contained less than 1 ppm fluoride.

What is claimed is:

1. A method of removing hydrogen fluoride (HF) from an HF containing hydrocarbon mixture comprising:
    contacting an HF adsorbent aluminum oxide containing resin, wherein the aluminum oxide containing resin contains less than 0.1 weight percent sulfur, with a HF containing hydrocarbon mixture forming a decontaminated hydrocarbon mixture; and
    collecting the decontaminated hydrocarbon mixture.

2. The method of claim 1, wherein the HF containing hydrocarbon mixture comprises C3 to C16 alkanes.

3. The method of claim 2, wherein the HF containing hydrocarbon mixture contains at least 99 percent C4 to C16 alkanes.

4. The method of claim 1, wherein the HF is present in the HF containing hydrocarbon mixture at a concentration of at least 300 ppm.

5. The method of claim 1, wherein the decontaminated hydrocarbon mixture contains less than 1 ppm or less of HF.

6. The method of claim 1, wherein the aluminum oxide containing resin contains at least 75% of activated alumina.

7. The method of claim 1, wherein the aluminum oxide containing resin contains at least 75% of a zeolite mineral.

8. The method of claim 1, wherein the aluminum oxide containing resin contains 25% or less of a clay binder.

9. The method of claim 1, wherein the HF containing hydrocarbon mixture is in contact with the aluminum oxide containing resin for an average residence time of from 10 minutes to 20 minutes.

10. A method for removing hydrogen fluoride (HF) from a HF containing hydrocarbon mixture comprising:
    feeding a HF containing hydrocarbon mixture to at least one treater vessel containing an aluminum oxide containing resin, wherein the aluminum oxide containing resin contains less than 0.1 weight percent sulfur; and
    pumping the HF containing hydrocarbon mixture through the at least one treater vessel at a flow rate of at least 50 gallons per minute (gpm) and at an ambient temperature, wherein the hydrocarbon mixture contacts the aluminum oxide containing resin at the ambient temperature adsorbing HF in the HF containing hydrocarbon mixture forming a treated hydrocarbon mixture.

11. The method of claim 10, wherein each of the at least one treater vessel has a pressure of from about 206 kpa to about 551 kpa.

12. The method of claim 10, wherein the HF containing hydrocarbon mixture flows through the at least one treater vessel with a residence time at least 10 minutes.

13. The method of claim 10, wherein the HF containing hydrocarbon mixture comprises C3 to C16 alkanes.

14. A method of removing hydrogen fluoride (HF) from an HF containing alkane mixture comprising:
    feeding an HF containing alkane mixture from a first storage tank through a pump into at least two treater vessels containing an aluminum oxide resin with less than 0.1 weight percent sulfur, wherein the at least two treatment vessels are connected in a serial configuration, the HF containing alkane mixture is fed into the at least two treater vessels at a flow rate at least 60 gallons per minute (gpm) under a pressure of at least 206 kpa at ambient temperature with an average residence time of contact with the aluminum oxide containing resin of at most 15 minutes; and
    collecting a treated alkane mixture from the at least two treater vessels into a second storage tank.

15. The method of claim 2, wherein the contaminated hydrocarbon mixture contains at least 13 percent C6 to C16 alkanes.

16. The method of claim 2, wherein the contaminated hydrocarbon mixture contains at least 55 percent C5 to C16 alkanes.

* * * * *